United States Patent
Wang (10) Patent No.: US 7,684,600 B2
(45) Date of Patent: Mar. 23, 2010

(54) METHOD AND APPARATUS FOR CALCULATING 3D VOLUME OF CEREBRAL HEMORRHAGE

(75) Inventor: Xueli Wang, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 784 days.

(21) Appl. No.: 11/564,502

(22) Filed: Nov. 29, 2006

(65) Prior Publication Data

US 2007/0167746 A1    Jul. 19, 2007

(30) Foreign Application Priority Data

Dec. 1, 2005    (CN) .................. 2005 1 0137354

(51) Int. Cl.
*G06K 9/00* (2006.01)
*A61B 5/05* (2006.01)

(52) U.S. Cl. ............... 382/128; 382/157; 382/132; 382/173; 382/154; 382/195; 600/425; 600/410; 600/398; 600/371; 600/407

(58) Field of Classification Search .......... 600/410, 600/425, 549, 504, 442, 438, 398, 371, 407; 382/173, 128, 132, 154, 131, 174, 157, 195; 324/312, 316, 300, 309

See application file for complete search history.

(56) References Cited

U.S. PATENT DOCUMENTS

| | | | | |
|---|---|---|---|---|
| 6,138,045 A | * | 10/2000 | Kupinski et al. | ............ 600/425 |
| 6,875,176 B2 | | 4/2005 | Mourad et al. | |
| 6,891,922 B2 | * | 5/2005 | Ferrant et al. | ................. 378/62 |
| 2002/0095087 A1 | * | 7/2002 | Mourad et al. | .............. 600/442 |
| 2003/0018244 A1 | | 1/2003 | Haddad et al. | |
| 2006/0079773 A1 | | 4/2006 | Mourad et al. | |

FOREIGN PATENT DOCUMENTS

| | | |
|---|---|---|
| JP | 2005-118510 | 5/2005 |
| JP | 2005118510 | * 5/2005 |

\* cited by examiner

*Primary Examiner*—Wesley Tucker
*Assistant Examiner*—Nancy Bitar
(74) *Attorney, Agent, or Firm*—Armstrong Teasdale LLP (57) ABSTRACT

The present invention provides a method and apparatus for appropriately calculating 3D volume of cerebral hemorrhage lesion. The present invention sets a ROI for normal cerebral parenchymal region and a ROI for cerebral hemorrhage lesion respectively for a plurality of continuous slice images obtained by imaging the head having cerebral hemorrhage onset with an X-ray CT device, determines a mean value of the CT values of pixels within the ROI of normal cerebral parenchymal region for each of a plurality of images, then determines an amount of shift of mean values of images based on the mean value of one image, adjusts the CT value of pixels in the ROI of cerebral hemorrhage lesion for each image by using the amount of shift for each image, specifies the maximum value of the adjusted CT value through a plurality of images, and then calculates the 3D volume of the cerebral hemorrhage lesion.

19 Claims, 4 Drawing Sheets

METHOD AND APPARATUS FOR CALCULATING 3D VOLUME OF CEREBRAL HEMORRHAGE

CROSS REFERENCE TO RELATED APPLICATIONS

This application claims the benefit of Chinese Application No. 200510137354.1 filed Dec. 1, 2005.

BACKGROUND OF THE INVENTION

The present invention is related to method and apparatus for calculating 3D volume of cerebral hemorrhage, in particular to method and apparatus for calculating 3D volume of cerebral hemorrhage based on X-ray CT (computed tomography) images of the head in which the intracerebral hemorrhage has been affected.

In order to diagnose and treat cerebral hemorrhage, 3D volume calculation of cerebral hemorrhage lesion is performed based on the X-ray CT images of the affected head. The 3D volume calculation of cerebral hemorrhage lesion is performed by identifying the location of cerebral hemorrhage on the image, then performing 3D volume calculation of identified lesion. The calculation methods consist of semi-automatic method (see for example patent reference 1) in which a specialist is involved in the segmentation of cerebral hemorrhage lesion, and fully automatic method in which everything is automatically performed from the identification of cerebral hemorrhage lesion to the 3D volume calculation.

[Patent reference 1] JP-A-2005-118510 (pp. 6 to 7, and FIGS. 3 to 8)

In a semi-automatic method, a specialist is involved in the segmentation of cerebral hemorrhage lesion, therefore requiring labor and time. Since the accuracy of the segmentation largely depends on the technical skill of the specialist, the result may be different among specialists and the reproducibility by a single specialist is not sufficient.

In contrast, fully automatic method is economic but has a problem in the segmentation accuracy, and does not yet provide a sufficient result. More specifically, this method has the tendency of under segmentation in the upper cerebral section and the tendency of over segmentation in the middle or lower cerebral section. Moreover, there may be cases that the section that has no cerebral hemorrhage is segmented, and that the cerebral hemorrhage lesion is not sufficiently segmented.

In both methods, the calculation ignores the partial volume effect and the CT value shift among a plurality of images so that the calculation result must be inaccurate.

SUMMARY OF THE INVENTION

Therefore, an object of the present invention is to provide a method and apparatus for calculating the 3D volume of cerebral hemorrhage lesion in an appropriate manner. Another object of the present invention is to provide a method and apparatus for calculating the 3D volume of cerebral hemorrhage lesion, which allows stable results to be obtained without the dependency on the technical skill of user.

Additionally, still another object of the present invention is to provide a method and apparatus for calculating 3D volume of cerebral hemorrhage lesion, which facilitate the user-friendly operation. Yet another object of the present invention is to provide a method and apparatus for calculation 3D volume of cerebral hemorrhage lesion, which accommodate to lower-, middle-, and upper-cerebral sections, and overcome the problems of partial volume effect and CT value shift among a plurality of images.

The invention in first aspect for solving the above-mentioned problems provides a method for calculating 3D volume of cerebral hemorrhage lesion comprising the steps of: setting ROI of normal cerebral parenchymal region and ROI of cerebral hemorrhage lesion, respectively, based on a plurality of images of continuous slices obtained by imaging the head affected by a cerebral hemorrhage by an X-ray CT device; determining mean value of CT values of pixels within said ROI of normal cerebral parenchymal region for a plurality of images; determining, based on the reference with the mean value of one image, the amount of shift of the mean value of any other images; using the shift value for each image to adjust the CT value of pixels within the ROI of the cerebral hemorrhage lesion for each image; specifying the maximum value of CT values after adjustment through a plurality of images; and calculating 3D volume of cerebral hemorrhage lesion given by the following equation:

$$3DVolume = \sum_{n=1}^{N} Index_n * f\left(\begin{array}{c} DFOV, SFOV, \\ SliceThickness, Magnification, \Lambda \end{array}\right)$$

if $Mean_1 < P_n \leq Maximum$, $Index_n = \dfrac{P_n - Mean_1}{Maximum - Mean_1}$ if $P_n \leq Mean_1$, $Index_n = 0$ where:

n: pixel number of pixel within the ROI of cerebral hemorrhage lesion in a plurality of images;

N: total number of pixels within the ROI of cerebral hemorrhage lesion in a plurality of images;

$p_n$: CT value after adjustment within the ROI of cerebral hemorrhage lesion;

DFOV: dimension of defined FOV;

SFOV: dimension of scanned FOV;

SliceThickness: thickness of a slice; and

Magnification: magnification value.

The invention in second aspect for solving the above-mentioned problems provides an apparatus for calculating 3D volume of cerebral hemorrhage lesion, comprising: a setting means for setting ROI of normal cerebral parenchymal region and ROI of cerebral hemorrhage lesion, respectively, based on a plurality of images of continuous slices obtained by imaging the head affected by a cerebral hemorrhage by an X-ray CT device; a mean value calculation means for determining mean value of CT values of pixels within said ROI of normal cerebral parenchymal region for a plurality of images; a shift value calculation means for determining, based on the reference with the mean value of one image, the amount of shift of the mean value of any other images; an adjustment means for using the shift value for each image to adjust the CT value of pixels within the ROI of the cerebral hemorrhage lesion for each image; a specifying means for specifying the maximum value of CT values after adjustment through a plurality of images; and a calculation means for calculating 3D volume of cerebral hemorrhage lesion given by the following equation:

$$3DVolume = \sum_{n=1}^{N} \text{Index}_n * f\left(\begin{array}{c} DEOV, SFOV, \\ SliceThickness, \text{Magnification}, \wedge \end{array}\right)$$

$$\text{if Mean}_1 < P_n \le \text{Maximum, Index}_n = \frac{P_n - \text{Mean}_1}{\text{Maximum} - \text{Mean}_1}$$

$$\text{if } P_n \le \text{Mean}_1, \text{Index}_n = 0$$

where:
- n: pixel number of pixel within the ROI of cerebral hemorrhage lesion in a plurality of images;
- N: total number of pixels within the ROI of cerebral hemorrhage lesion in a plurality of images;
- $p_n$: CT value after adjustment within the ROI of cerebral hemorrhage lesion;
- DFOV: dimension of defined FOV;
- SFOV: dimension of scanned FOV;
- SliceThickness: thickness of a slice; and
- Magnification: magnification value.

It is preferable to eliminate the bone section included within the ROI of cerebral hemorrhage lesion, in order to obtain a correct result. It is also preferable to eliminate the foreign part included within the ROI of cerebral hemorrhage lesion, in order to obtain a correct result.

In accordance with the aspects described above of the present invention, the present invention allows to provide a method and apparatus for appropriately calculating 3D volume of cerebral hemorrhage lesion, by: setting ROI of normal cerebral parenchymal region and ROI of cerebral hemorrhage lesion, respectively, based on a plurality of images of continuous slices obtained by imaging the head affected by a cerebral hemorrhage by an X-ray CT device; determining mean value of CT values of pixels within said ROI of normal cerebral parenchymal region for a plurality of images; determining, based on the reference with the mean value of one image, the amount of shift of the mean value of any other images; using the shift value for each image to adjust the CT value of pixels within the ROI of the cerebral hemorrhage lesion for each image; specifying the maximum value of CT values after adjustment through a plurality of images; and calculating 3D volume of cerebral hemorrhage lesion given by the following equation:

$$3DVolume = \sum_{n=1}^{N} \text{Index}_n * f\left(\begin{array}{c} DEOV, SFOV, \\ SliceThickness, \text{Magnification}, \wedge \end{array}\right)$$

$$\text{if Mean}_1 < P_n \le \text{Maximum, Index}_n = \frac{P_n - \text{Mean}_1}{\text{Maximum} - \text{Mean}_1}$$

$$\text{if } P_n \le \text{Mean}_1, \text{Index}_n = 0$$

where:
- n: pixel number of pixel within the ROI of cerebral hemorrhage lesion in a plurality of images;
- N: total number of pixels within the ROI of cerebral hemorrhage lesion in a plurality of images; $p_n$: CT value after adjustment within the ROI of cerebral hemorrhage lesion;
- DFOV: the dimension of defined FOV;
- SFOV: the dimension of scanned FOV;
- SliceThickness: thickness of a slice; and
- Magnification: magnification value.

In accordance with the aspects described above of the present invention, the present invention allows to provide a method and apparatus for calculating 3D volume of cerebral hemorrhage lesion, which may obtain stable results without the dependency to the technical skill of the user. In addition, in accordance with the aspects described above of the present invention, the present invention allows to provide a method and apparatus for calculating 3D volume of cerebral hemorrhage lesion, which facilitate the user-friendly operation.

In accordance with the aspects described above of the present invention, the present invention allows to provide a method and apparatus for calculating 3D volume of cerebral hemorrhage lesion, which may accommodate to lower-, middle-, and upper-cerebral sections, and overcome the problems of partial volume effect and CT value shift among a plurality of images.

Further objects and advantages of the present invention will be apparent from the following description of the preferred embodiments of the invention as illustrated in the accompanying drawings.

DETAILED DESCRIPTION OF THE INVENTION

Figure 1:
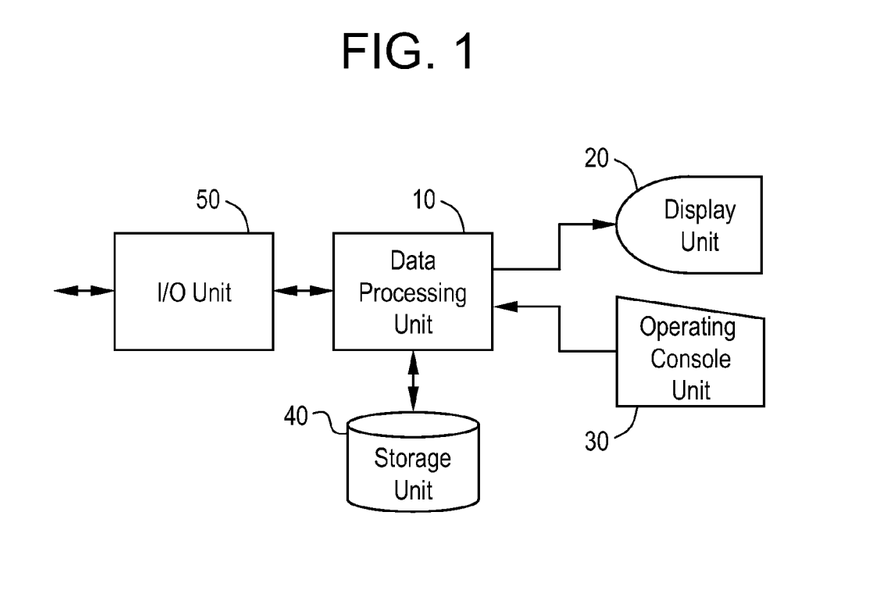
FIG. 1 shows a schematic diagram of the overview of an embodiment of image processing apparatus in accordance with the best mode for carrying out the invention.

A best mode for carrying out the invention will be described in greater details herein below with reference to accompanying drawings. It is to be understood that the present invention is not limited to the best mode for carrying out the invention. FIG. 1 shows a schematic block diagram illustrating an image processing apparatus.

The apparatus shown is an exemplary embodiment of the best mode for carrying out the invention. The structure of the apparatus indicates an exemplary embodiment of the best mode for carrying out the invention of the apparatus for calculating 3D volume of cerebral hemorrhage lesion. The operation of the apparatus indicates an exemplary embodiment of the best mode for carrying out the invention of the method for calculating 3D volume of cerebral hemorrhage lesion.

As shown in FIG. 1, the apparatus includes a data processing unit 10, a display unit 20, an operating console unit 30, a storage unit 40, and an I/O unit 50. The data processing unit 10 will perform predetermined data processing on the data stored in the storage unit 40, based on the interactive operation by the user through the display unit 20 and the operating console unit 30. The data processing unit 10 will also perform data input/output from/to an external device through the I/O unit 50.

The X-ray CT images that are used for the calculation of 3D volume of cerebral hemorrhage lesion are input from an external device through the I/O unit 50. The X-ray CT images are a plurality of images of continuous slice. The X-ray CT images will be referred to as simply images, herein below.

The external device may include for example an X-ray CT apparatus, and a medical image server. The apparatus of the present invention may be part of such X-ray CT apparatus or medical image server. In this case the I/O unit 50 is not necessarily required.

Figure 2:
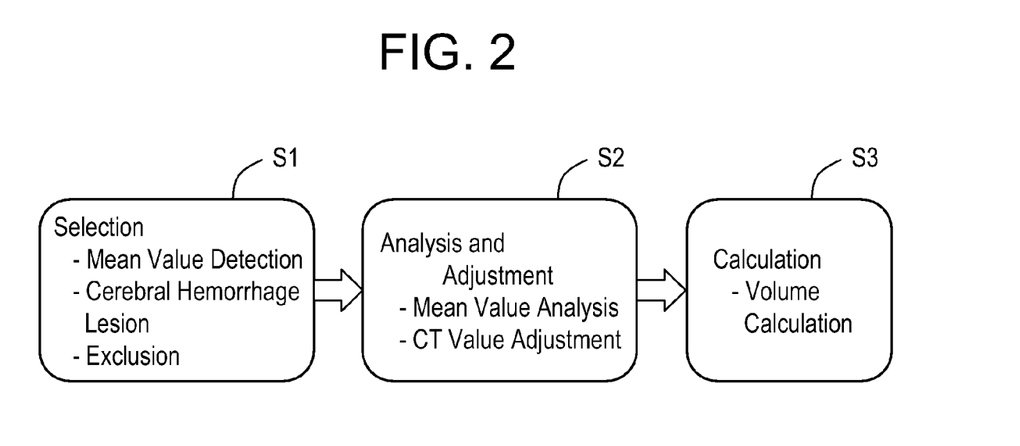
FIG. 2 shows a schematic diagram of a process for calculating the 3D volume of cerebral hemorrhage lesion.

The calculation of 3D volume of cerebral hemorrhage lesion to be performed by the inventive apparatus will be described now. FIG. 2 shows a schematic diagram of the process of calculation of 3D volume of cerebral hemorrhage lesion. As shown in FIG. 2, the process of calculation of 3D volume of cerebral hemorrhage lesion is comprised of three processes, namely S1, S2, and S3.

Process S1 is the selection process. In the selection process S1, the selection of the section used for the detection of mean value, selection of the cerebral hemorrhage lesion, and selection of the section to be removed, are performed. The selection of the section of elimination is performed when required. The details of the selection process S1 will be described in greater details later.

Process S2 is the analysis and adjustment process. In the analysis and adjustment process S2, mean value of CT values is analyzed and CT values are adjusted. The details of the analysis and adjustment process S2 will be described in greater details later.

Process S3 is the calculation process. In the calculation process S3 the 3D volume is calculated. The volume calculation derives the total 3D volume of the cerebral hemorrhage lesion. The calculation process S3 will be described in greater details later.

Figure 3:
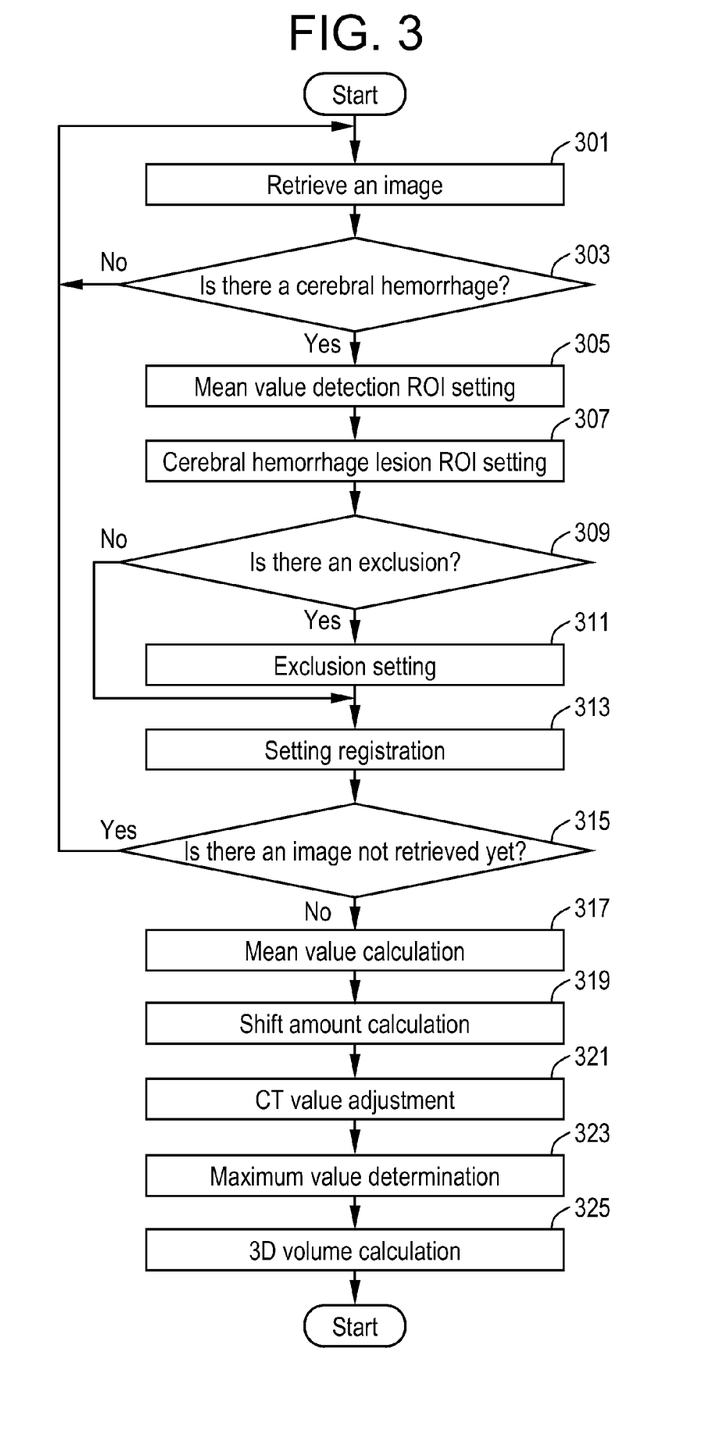
FIG. 3 shows a flow chart of the operation of an embodiment of image processing apparatus in accordance with the best mode for carrying out the invention.

FIG. 3 shows a flow chart of the operation of the apparatus. In step 301, an image is retrieved. The image retrieval is performed by the operation of the operating console unit 30 by the user. Through the image retrieval, the first one of a plurality of images is displayed on the display unit 20.

In step 303 the displayed image is determined whether the cerebral hemorrhage is present or not. The determination whether the cerebral hemorrhage is present or not is performed by visual observation of the user. If it is determined that the cerebral hemorrhage is not present, then the step goes back to step 301 to retrieve another image. While the cerebral hemorrhage is not present, the operation is iteratively repeated between step 301 and 303.

Once it is determined that the cerebral hemorrhage is present. In step 305, ROI (region of interest) for detecting mean value is set. The setting of ROI for detecting mean value is performed for determining the mean value of CT values in normal cerebral parenchymal region in the image.

Figure 4:
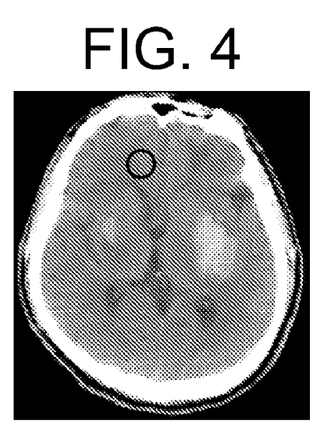
FIG. 4 shows a gray scale photograph indicating an embodiment of the mean value detection ROI setting.

FIG. 4 shows an example of the ROI setting for detecting mean value. As shown in FIG. 4, a circular ROI is set to a region that has not cerebral hemorrhage in the normal cerebral parenchymal region. The ROI setting can be performed by clicking on the desired section of the image by the user using a pointing device of the operating console unit 30. The surface area of the ROI is predefined. The mean value detecting ROI can be predefined in a plurality of images. The operating console unit 30 is an exemplary embodiment of the setting means in accordance with the present invention.

Figure 5:
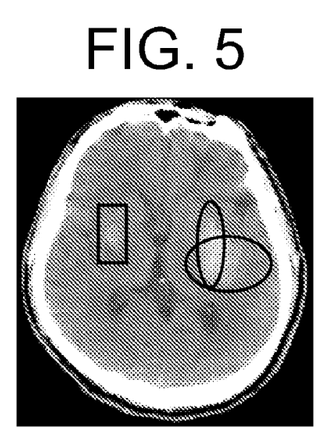
FIG. 5 shows a gray scale photograph indicating an embodiment of the cerebral hemorrhage lesion ROI setting.

Next, in step 307, a ROI is set for cerebral hemorrhage lesion. The cerebral hemorrhage ROI setting is performed for identifying the cerebral hemorrhage lesion on the image. FIG. 5 shows an exemplary embodiment of cerebral hemorrhage lesion ROI setting. As shown in FIG. 5, a ROI of an appropriate figure such as an ellipse or rectangle is set so as to encompass the cerebral hemorrhage lesion.

The ROI setting is performed such as by the user clicking on a desired point on the image with the pointing device of the operating console unit 30 to develop a ROI figure, then adjusting the position, shape, size, inclination and the like of the figure so as to encompass the cerebral hemorrhage lesion. The operating console unit 30 is an exemplary embodiment of the setting means in accordance with the present invention.

Since the cerebral hemorrhage lesion ROI is sufficient to encompass the cerebral hemorrhage lesion, thus the contour of the cerebral hemorrhage lesion is not necessarily needed to be traced precisely. In addition, as shown in FIG. 5, a plurality of ROIs encompassing one single cerebral hemorrhage lesion can be set. This facilitates the ROI setting as well as saving the labor and time. The ROI setting is therefore user friendly, while at the same time accommodating to any of lower-, middle-, and upper-cerebral sections without difficulty. Furthermore, the setting is not dependent on the technical skill of the user.

Figure 6:
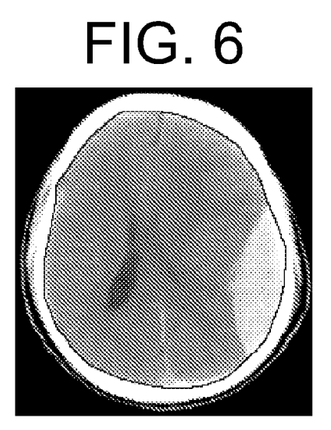
FIG. 6 shows a gray scale photograph indicating an embodiment of the cerebral hemorrhage lesion ROI setting.

The cerebral hemorrhage ROI is set so as not to include any osseous portion. As shown in FIG. 6 for example, such setting is difficult when the cerebral hemorrhage lesion resides immediately adjacent to a cranial bone, a ROI is to be set to include some osseous portion. In such case the difference between CT values is used to detect the boundary between the cerebral hemorrhage lesion and the cranial bone to set the inside of boundary as the cerebral hemorrhage lesion ROI. The detection of boundary between the cerebral hemorrhage lesion and the cranial bone is automatically performed by a known algorithm in the data processing unit 10. The data processing unit 10 is an exemplary embodiment of the osseous portion elimination means in accordance with the present invention.

Then, in step 309, it is determined whether a region to be eliminated is present or not. The determination of the presence of elimination region is performed by the visual observation by the user. The elimination region is a bright region, which is explicitly not a cerebral hemorrhage, including for example any artificial implantation residing in the brain by a surgical intervention, and spontaneous calcification.

Figure 7:
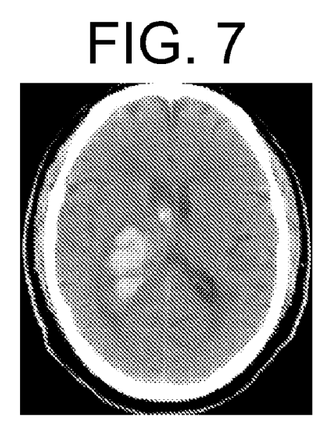
FIG. 7 shows a gray scale photograph indicating an embodiment of the excluding setting.

When there is an elimination region, in step 311, an elimination setting is performed. An exemplary elimination setting is shown in FIG. 7. The rectangular area shown in FIG. 7 is the elimination region. The elimination region setting is performed by tracing the contour of the object to be removed with the pointing device of the operating console unit 30. The elimination region setting is an exceptional process only when there is an object to be eliminated, and is unlikely to be frequent. The operating console unit 30 is an exemplary embodiment of the foreign part elimination means in accordance with the present invention.

Figure 8:
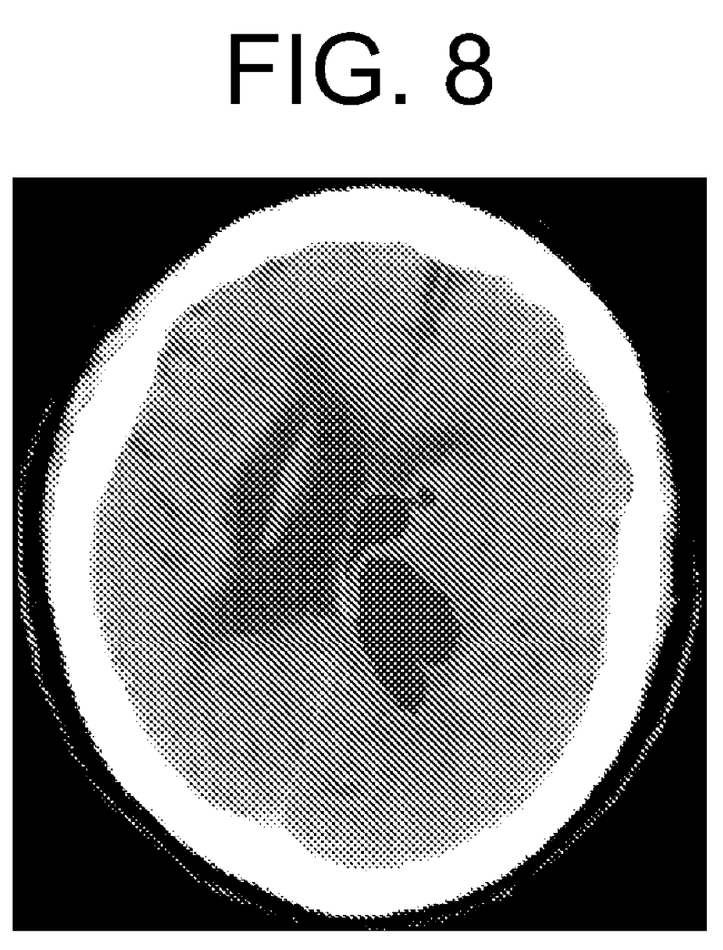
FIG. 8 shows a gray scale photograph indicating a computed tomography of brain.

There may be, as a special case, as shown in FIG. 8, bleeding retained in the cerebral ventricle. This is not hemorrhage in the normal cerebral parenchymal region so that the volume calculation will ignore the bleeding. In the conventional, fully automatic method, a malfunction may be appeared, however in the apparatus in accordance with the present invention, the user determination by visual confirmation allows such incident as described above to be readily avoided.

In step 313 the setting is registered. The contents of the mean value detection ROI setting and the cerebral hemorrhage lesion ROI setting will be stored in the storage unit 40.

The elimination setting, if any, will be also registered. This defines the mean value detection ROI setting and the cerebral hemorrhage lesion ROI setting (as well as the elimination setting) for an image.

In step 315 it is determined whether there is still an image that is not retrieved, and if there is an image not retrieved, the process returns to step 301 to retrieve the image, and applies the processing of steps 303 to 313 to the image. This operation is iteratively repeated until there is no longer an image that is not retrieved. In this manner the mean value detection ROI setting and the cerebral hemorrhage lesion ROI setting (as well as the elimination setting) for each image are defined for all of a plurality of images. The steps 303 to 315 correspond to the selection process S1 shown in FIG. 2.

In step 317 mean value is calculated. The mean value calculation is performed in the data processing unit 10. The data processing unit 10 is an exemplary embodiment of the mean value calculation means in accordance with the present invention. The data processing unit 10 determines the mean value of CT values in the mean value detecting ROI for each image. This yields the mean value as shown below:

$$\{Mean_i, i=1, 2, 3, \Lambda, I\}$$

where:
i: number of image
I: largest number of images.

In step 319 the amount of shifting is calculated. The shift calculation is performed in the data processing unit 10. The data processing unit 10 is an exemplary embodiment of the shift amount calculation means in accordance with the present invention. The data processing unit 10 decomposes the mean value of each image to the sum of a reference mean value and an amount of shift, using the following equation:

$$Mean_i = Mean_1 + \Delta_i, i=1, 2, 3, \Lambda, I$$

As the reference mean value, the mean value of for example first image is used. It should be noted that the mean value of any one of a plurality of images may be used for the reference mean value.

In step 321, the CT value is adjusted. The CT value adjustment is performed in the data processing unit 10. The data processing unit 10 is an exemplary embodiment of the adjustment means in accordance with the present invention. The data processing unit 10 adjusts the CT value of every pixel in the cerebral hemorrhage lesion ROI by using the amount of shift. The CT value adjustment is performed for each image, using the following equation:

$$Pixel_{mi} = Pixel_{mi} - \Delta_i, i=1, 2, 3, \Lambda, I$$

where:
i: number of image
m: pixel number in a same image

The CT value adjustment as have been described above will adjust the amount of CT value shift among a plurality of images to homogenize the pixel value condition in the mean value detection ROI of all images.

Next, in step 323, maximum value is specified. The maximum value specification is performed in the data processing unit 10. The data processing unit 10 specifies the maximum value of the pixel values of adjusted CT values for each cerebral hemorrhage lesion ROI to identify the largest one of those maximum values. The maximum value of each ROI and the maximum value among a plurality of ROIs are respectively obtained.

$$\{Max_j, j=1, 2, 3, \Lambda, J\}$$

$$Maximum = Max(Max_j, j=1, 2, 3, \Lambda, J)$$

where:
j: ROI number
J: maximum ROI number

Steps 317 to 323 correspond to the analysis and adjustment process S2 shown in FIG. 2.

In step 325, the 3D volume is calculated. The step 325 corresponds to the calculation process S3 shown in FIG. 2. The 3D volume calculation is performed by the data processing unit 10. The data processing unit 10 determines at first the volume of one single pixel. The 3D volume of one single pixel can be determined by the following equation:

$$f(DFOV, SFOV, SliceThickness, Magnification, \Lambda)$$

where:
DFOV: the size of defined FOV
SFOV: the size of scan FOV
SliceThickness: the thickness of a slice
Magnification: magnification The data processing unit 10 then sorts the pixel value of adjusted CT value in the ascending order of CT value through a plurality of images. This yields a sequence as shown in the following equation:

$$Vector = (P_n, n=1, 2, 3, \Lambda, N)$$

where
$p_n$: pixel value of adjusted CT value
n: pixel number through a plurality of images
N: total number of pixels in a plurality of images The data processing unit 10 then determines the maximum value in a pixel value group as follows:

$$P_N = Maximum$$

The data processing unit 10 is an exemplary embodiment of the specifying means in accordance with the present invention.

The data processing unit 10 then calculates the 3D volume using the following equation. The data processing unit 10 is an exemplary embodiment of calculation means in accordance with the present invention.

$$3DVolume = \sum_{n=1}^{N} Index_n * f\begin{pmatrix} DFOV, SFOV, \\ SliceThickness, Magnification, \Lambda \end{pmatrix}$$

if $Mean_1 < P_n \leq Maximum$, $Index_n = \dfrac{P_n - Mean_1}{Maximum - Mean_1}$ if $P_n \leq Mean_1$, $Index_n = 0$ The above equation is a weighted addition of pixel volumes. The weight index is the normalized difference between the CT value of pixel and the reference mean value by the difference between the maximum value and the reference mean value. The weight index of the pixel that has a CT value less than the reference mean value is 0.

Therefore, the weight index of the pixel that has the maximum CT value will be 1, the weight index of the pixel that has a CT value less than the reference mean value will be 0, and the weight index of the pixels that have a CT value between the maximum value and the reference mean value will be a value between 1 and 0.

As the result of the weighting, the pixels that contribute to the 3D volume calculation are only those that have a CT value more than the reference mean value. The contribution will be the largest at the pixel having the largest CT value, and will be lesser in correspondence with the distance from the largest value.

The decrease of contribution indicates the degrees of partial volume effect. The above equation has been devised to calculate the 3D volume with less contribution of the pixels that have more partial volume effect, so as to be reasonable for the 3D volume calculation of the cerebral hemorrhage lesion. It is also reasonable for the contribution of the pixels that have a CT value less than the reference mean value to be 0.

In addition, even when a pixel value contains noises, the sum of all values will cancel so that the noises will have significantly low effect. The 3D volume calculated in accordance with the above equation therefore indicates the accurate volume of the cerebral hemorrhage lesion along with the effect of the CT value adjustment.

Many widely different embodiments of the invention may be configured without departing from the spirit and the scope of the present invention. It should be understood that the present invention is not limited to the specific embodiments described in the specification, except as defined in the appended claims.

The invention claimed is:

1. A method for calculating 3D volume of cerebral hemorrhage lesion, comprising the steps of:
setting ROI of normal cerebral parenchymal region and ROI of cerebral hemorrhage lesion, respectively, based on a plurality of images of continuous slices obtained by imaging a head affected by a cerebral hemorrhage by an X-ray CT device;
determining mean value of CT values of pixels within said ROI of normal cerebral parenchymal region for a plurality of images;
determining, based on the reference with the mean value of one image, the amount of shift of the mean value of any other images;
using the shift value for each image to adjust the CT value of pixels within the ROI of the cerebral hemorrhage lesion for each image;
specifying the maximum value of CT values after adjustment through a plurality of images; and
calculating 3D volume of cerebral hemorrhage lesion given by the following equation:

$$3DVolume = \sum_{n=1}^{N} Index_n * f\left(\begin{array}{c} DFOV, SFOV, \\ SliceThickness, Magnification, \Lambda \end{array}\right)$$ [equation 1]

$$\text{if } Mean_1 < P_n \le Maximum, Index_n = \frac{P_n - Mean_1}{Maximum - Mean_1}$$

$$\text{if } P_n \le Mean_1, Index_n = 0$$

where:
n: pixel number of pixel within the ROI of cerebral hemorrhage lesion in a plurality of images;
N: total number of pixels within the ROI of cerebral hemorrhage lesion in a plurality of images;
$p_n$: CT value after adjustment within the ROI of cerebral hemorrhage lesion;
DFOV: dimension of defined FOV;
SFOV: dimension of scanned FOV;
SliceThickness: thickness of a slice; and
Magnification: magnification value.

2. A method for calculating 3D volume of cerebral hemorrhage lesion according to claim 1 further comprising the step of:
excluding an osseous portion included in the ROI of cerebral hemorrhage lesion.

3. A method for calculating 3D volume of cerebral hemorrhage lesion according to claim 1 further comprising the step of:
excluding a foreign part included in the ROI of cerebral hemorrhage lesion.

4. An apparatus for calculating 3D volume of cerebral hemorrhage lesion, comprising:
a setting device for setting ROI of normal cerebral parenchymal region and ROI of cerebral hemorrhage lesion, respectively, based on a plurality of images of continuous slices obtained by imaging the head affected by a cerebral hemorrhage by an X-ray CT device;
a mean value calculation device for determining mean value of CT values of pixels within said ROI of normal cerebral parenchymal region for a plurality of images;
a shift value calculation device for determining, based on the reference with the mean value of one image, the amount of shift of the mean value of any other images;
an adjustment device for using the shift value for each image to adjust the CT value of pixels within the ROI of the cerebral hemorrhage lesion for each image;
a specifying device for specifying the maximum value of CT values after adjustment through a plurality of images; and
a calculation device for calculating 3D volume of cerebral hemorrhage lesion given by the following equation:

$$3DVolume = \sum_{n=1}^{N} Index_n * f\left(\begin{array}{c} DFOV, SFOV, \\ SliceThickness, Magnification, \Lambda \end{array}\right)$$ [equation 2]

$$\text{if } Mean_1 < P_n \le Maximum, Index_n = \frac{P_n - Mean_1}{Maximum - Mean_1}$$

$$\text{if } P_n \le Mean_1, Index_n = 0$$

where:
n: pixel number of pixel within the ROI of cerebral hemorrhage lesion in a plurality of images;
N: total number of pixels within the ROI of cerebral hemorrhage lesion in a plurality of images;
$p_n$: CT value after adjustment within the ROI of cerebral hemorrhage lesion;
DFOV: dimension of defined FOV;
SFOV: dimension of scanned FOV;
SliceThickness: thickness of a slice; and
Magnification: magnification value.

5. An apparatus for calculating 3D volume of cerebral hemorrhage lesion according to claim 4, further comprising:
an osseous portion excluding device for excluding the osseous portion included in the ROI of cerebral hemorrhage lesion.

6. An apparatus for calculating 3D volume of cerebral hemorrhage lesion according to claim 4, further comprising:
a foreign part excluding device for excluding the foreign part included in the ROI of cerebral hemorrhage lesion.

7. A method for calculating 3D volume of cerebral hemorrhage lesion, said method comprising
retrieving a first image;
selecting a first region of interest (ROI) within the first image that does not include a cerebral hemorrhage lesion selecting a second region of interest (ROI) within the first image that includes the cerebral hemorrhage lesion;

calculating a mean value of a plurality of pixels within the first region of interest;

determining, using the calculated mean value, the amount of shift of the mean value of at least one subsequent image;

using the determined shift value to adjust the CT value of pixels within the first region of interest within the first and subsequent images; and calculating a three-dimensional volume of the cerebral hemorrhage lesion after the CT values of at least the first and subsequent images has been adjusted;

and calculating the three-dimensional volume of the cerebral hemorrhage lesion in accordance with $$3DVolume = \sum_{n=1}^{N} Index_n * f(DFOV, SFOV, SliceThickness, Magnification, \Lambda)$$

$$Index_n = \frac{P_n - Mean_1}{Maximum - Mean_1} \text{ if } Mean_1 < P_n \leq Maximum,$$
$$\text{if } P_n \leq Mean_1, Index_n = 0$$

where:

n: pixel number of pixel within the ROI of cerebral hemorrhage lesion in a plurality of images;

N: total number of pixels within the ROI of cerebral hemorrhage lesion in a plurality of images;

Pn: CT value after adjustment within the ROI of cerebral hemorrhage lesion

DFOV: dimension of defined FOV;

SFOV: dimension of scanned FOV;

SliceThickness: thickness of a slice; and

Magnification: magnification value.

8. A method in accordance with claim 7, wherein retrieving an image further comprises retrieving a computed tomography image.

9. A method in accordance with claim 7, first comprising determining if a cerebral hemorrhage legion is present within the retrieved image using a visual observation prior to selecting the second region of interest.

10. A method in accordance with claim 7, further comprising retrieving a second image if it is determined that a cerebral hemorrhage lesion is not present in the retrieved image.

11. A method in accordance with claim 7, further comprising further comprising adjusting at least one of a position, a size, a shape, and an inclination of the second region of interest area until the cerebral hemorrhage lesion is substantially within the second region of interest area.

12. A method in accordance with 7, further comprising selecting a plurality of region of interests (ROI) within the first image, wherein each selected region of interest includes at least a portion of the cerebral hemorrhage lesion.

13. A method in accordance with claim 7, wherein selecting the second region of interest further comprises selecting the second region of interest such that the second region of interest does not include an osseous portion.

14. A method in accordance with claim 7, further comprising:

visually identifying a third region of interest within the retrieved image that is not explicitly a cerebral hemorrhage lesion; and removing the third region of interest.

15. A method in accordance with claim 14, further comprising:

tracing a contour around the periphery of the visually identified region; and removing the portion of the retrieved image included within the traced contour.

16. A method in accordance with claim 7, further comprising excluding a foreign part included in the second region of interest.

17. A method in accordance with claim 7, wherein calculating a mean value of a plurality of pixels further comprises calculating a mean value of a plurality of pixels in accordance with $$\{Mean_i, i=1, 2, 3, \Lambda, I\}$$

where:

i: number of image

I: largest number of images.

18. A method in accordance with claim 7, further comprising specifying the maximum value of the pixel values of adjusted CT values in the second region of interest to identify the largest one of those maximum values.

19. A method in accordance with claim 18, further comprising adjusting the amount of CT value shift among a plurality of images to homogenize the pixel value condition in the second region of interest for a plurality of image.

* * * * *